(12) United States Patent
Grigorian et al.

(10) Patent No.: US 9,474,729 B2
(45) Date of Patent: *Oct. 25, 2016

(54) TOPICAL ANTIMICROBIAL COMPOSITIONS AND METHODS OF USING SAME

(75) Inventors: Irina Grigorian, Bridgewater, NJ (US); Manfred F. Dyck, Far Hills, NJ (US); Rainer Gruening, Basking Ridge, NJ (US)

(73) Assignee: HYDROMER, INC., Branchburg, NJ (US)

( * ) Notice: Subject to any disclaimer, the term of this patent is extended or adjusted under 35 U.S.C. 154(b) by 169 days.

This patent is subject to a terminal disclaimer.

(21) Appl. No.: 12/930,786

(22) Filed: Jan. 14, 2011

(65) Prior Publication Data

US 2011/0230474 A1 Sep. 22, 2011

Related U.S. Application Data

(60) Provisional application No. 61/336,074, filed on Jan. 14, 2010.

(51) Int. Cl.
| | |
|---|---|
| *A01N 37/18* | (2006.01) |
| *A01N 51/00* | (2006.01) |
| *A61K 31/63* | (2006.01) |
| *A01N 37/00* | (2006.01) |
| *A61K 31/19* | (2006.01) |
| *A61K 31/136* | (2006.01) |
| *A61K 9/00* | (2006.01) |
| *A61K 9/08* | (2006.01) |
| *A61K 31/5415* | (2006.01) |

(52) U.S. Cl.
CPC ........... *A61K 31/136* (2013.01); *A61K 9/0017* (2013.01); *A61K 9/08* (2013.01); *A61K 31/5415* (2013.01)

(58) Field of Classification Search
CPC ..... A61K 31/136; A61K 9/0017; A61K 9/08
USPC .................................................. 514/155, 2.4
See application file for complete search history.

(56) References Cited

U.S. PATENT DOCUMENTS

| | | | | |
|---|---|---|---|---|
| 4,548,807 A | * | 10/1985 | Westfall et al. | 424/45 |
| 5,000,954 A | * | 3/1991 | Stadtmueller | 424/770 |
| 5,763,412 A | * | 6/1998 | Khan et al. | 514/23 |
| 5,774,909 A | * | 7/1998 | Stable | 4/622 |
| 5,780,064 A | * | 7/1998 | Meisters et al. | 424/616 |
| 6,168,794 B1 | * | 1/2001 | Reusser et al. | 424/769 |
| 6,458,391 B1 | | 10/2002 | Reusser et al. | |
| 6,699,510 B2 | | 3/2004 | McSherry et al. | |
| 2003/0078242 A1 | | 4/2003 | Raad et al. | |
| 2005/0013836 A1 | | 1/2005 | Raad | |
| 2005/0197634 A1 | | 9/2005 | Raad et al. | |
| 2005/0226826 A1 | | 10/2005 | Eason et al. | |
| 2006/0062829 A1 | | 3/2006 | Simonson et al. | |
| 2007/0027119 A1 | * | 2/2007 | Ahmed et al. | 514/159 |
| 2007/0074672 A1 | | 4/2007 | Torgerson et al. | |
| 2007/0167379 A1 | * | 7/2007 | Hacket et al. | 514/28 |
| 2007/0298085 A1 | | 12/2007 | Lestage et al. | |
| 2008/0145390 A1 | * | 6/2008 | Taylor et al. | 424/405 |
| 2008/0196674 A1 | | 8/2008 | Buck et al. | |
| 2008/0201871 A1 | | 8/2008 | Sun et al. | |
| 2008/0216762 A1 | | 9/2008 | Gerk et al. | |
| 2010/0234460 A1 | * | 9/2010 | Foret et al. | 514/558 |

FOREIGN PATENT DOCUMENTS

WO    WO 2008031087 A1 *    3/2008

OTHER PUBLICATIONS

Narat "Brilliant Green: A Clinical Study of Its Value as a Local Antiseptic." Annals of Surgery 94.6 (1931): 1007-1012.*
Manske et al. "Topical treatment of digital dermatitis associated with severe heel-horn erosion in a Swedish dairy herd." Preventive veterinary medicine 53.3 (2002):215-231.*

* cited by examiner

*Primary Examiner* — Layla Soroush
(74) *Attorney, Agent, or Firm* — Hoffmann & Baron, LLP

(57) ABSTRACT

The invention includes a method of treating a mammal comprising topically applying an aqueous composition to a target site on the mammal, wherein the aqueous composition comprises: active ingredients comprising i) a cosmetic dye selected from a violet, blue or green dye, or combinations thereof, and ii) an enhancing ingredient, wherein the relative weight percentage of the cosmetic dye to the enhancing ingredient is about 1:2 to about 40:1, wherein the cosmetic dye interacts with keratinous material thereby i) substantially staining the target site and ii) inhibiting the active ingredients from significantly leaching from the target site.

3 Claims, No Drawings

TOPICAL ANTIMICROBIAL COMPOSITIONS AND METHODS OF USING SAME

CROSS-REFERENCE TO RELATED APPLICATION

This application claims the benefit of U.S. Provisional Application No. 61/336,074, filed Jan. 14, 2010, which is incorporated herein by reference in its entirety.

BACKGROUND OF THE INVENTION

The present invention relates to compositions and methods of providing rapid and persistent control of a broad-spectrum of microbes on mammalian surfaces by topical application of compositions.

Lameness of diary cows and sheep is one of the major problems facing the dairy and meat industry, respectively, today. The cost of lameness is measured by lost milk production, culled cows, underweight meat animals, additional labor, veterinary bills, and medicines for treatment. In the United States, the annual overall cost of lameness is estimated to exceed 570 million dollars. It is especially a problem in large herds, which are the fastest growing segment of the market. The prevalence of lameness in large herds is 50% or more.

Lameness is, in many cases, caused by anaerobic organisms such as *Arcanobacterium pyogenes* (previously called *Corynebacterium pyogenes*), in particular where the infection goes into the deep structure of the hoof. In sheep the infection may be accompanied by swelling and a white to black pus discharge.

There are multiple causes for lameness ranging from lack of general stable hygiene, specific hoof hygiene, hoof care, malnutrition, general genetic disposition, specific genetic defects to bacterial and viral infections. For example, fibroma (corns) is a genetic condition found in cattle which causes a hard, fibrous lump to form between the claws of the foot. The corn makes the hoof more susceptible to subsequent bacterial and viral infections. These infections occur at various locations in and around the hooves of the cattle.

In addition to the general lesions caused by infection, a disease of unknown etiology has been spreading throughout the western United States. This disease is digital dermatitis. Digital dermatitis is characterized by painful lesions, which often are surrounded by a ridge of hyperkeratotic (thickened) skin with finger like projections. Due to its appearance, the disease is commonly referred to as hairy wart or strawberry disease; it is also known as Mortellaro disease.

Studies have shown that a third of all lameness in cows is caused by digital dermatitis. Digital dermatitis is present worldwide and is estimated to be present in 41% of herds smaller than 100 cows, and from 64% to 82% in larger herds.

Other contagious and debilitating diseases of the bovine foot and hoof include such conditions as bovine hoof rot and interdigital dermatitis. In addition to causing lameness in diary cows, these contagious diseases also cause a significant decrease in milk production and sometimes death. Dairy farmers report as much as 50% less milk being produced per cow. (Linda Leake, Farm Journal, Inc., (1998).) In sheep, in addition to causing lameness and reduced production, foot rot is highly contagious sometimes resulting in a whole flock becoming infected. (Government of Newfoundland and Labarador 2004)

For years, directing animals through hoof baths containing hoof care solutions has been practiced as an aid to general hoof health and hygiene for the prevention of, and a cure for, diseases of the animals' hooves. Materials used for these solutions include copper sulfate, zinc sulfate, formaldehyde, quaternary ammonium compounds, peroxides, organic acids, and their combinations, and certain antibiotics. Additionally, several over the counter commercially compounded liquid products have been and are being used. Major manufacturers of this latter category are Delaval (DoubleAction), Westfalia-Surge (Pedicure Rx), and SSI Corporation (Healthy Foot). Copper sulfate, zinc sulfate and other heavy metal based antimicrobials are usually applied in 5% to 10% solutions to be effective.

Recently, the negative environmental impact of the use of heavy metal compounds has been recognized. Efforts have been made to use mixed salts in combination with specific additives in order to reduce the overall use of heavy metal (to concentrations as low as low as 0.5%). However, despite regulatory restrictions, heavy metals are still in use since no effective alternative products are presently on the market.

Hoof baths are generally located in the return alley of dairy milking barns or parlors. After being milked, the animals typically walk through the hoof bath on the way back to where they are housed. The feet and hooves will typically contain accumulated dirt and manure. This is especially true in modern dairy facilities with housing contained in limited areas such as free stall or tie stall barns or dry lots instead of open pasture.

In addition, on passing through the hoof bath, the cows may defecate into the hoof bath. The added organic material or load to the hoof bath compromises the antimicrobial products' ability to work in the disinfection and cleansing of the cow hooves where the causative microorganisms are located. For economic reasons, the use of antibacterial chemical and biological products in doses high enough to compensate for the organic material present in the hoof bath and to penetrate through organic material and whatever tissue may conceal or otherwise harbor the bacterial pathogens, is usually cost prohibitive. Other chemical products that are less expensive to use at higher doses have the disadvantage in that they may be toxic to the animals, to the people working in the dairy facilities, and, particularly, to the environment. Heavy metal moieties of the compounds do not break down and accumulate in the environment.

Accordingly, there is a need for a more effective and environmentally friendly manner by which to treat and prevent hoof diseases in bovine livestock. In particular, a need exists for an effective method to control a broad spectrum of microbes that is fast-acting, has long-lasting efficacy, and is mild to livestock.

SUMMARY OF THE INVENTION

In one aspect, the present invention provides a method of treating a mammal comprising topically applying an aqueous composition to a target site on the mammal, wherein the aqueous composition comprises: active ingredients comprising i) a cosmetic dye selected from a violet, blue or green dye, or combinations thereof, and ii) an enhancing ingredient, wherein the cosmetic dye interacts with keratinous material thereby i) substantially staining the target site and ii) inhibiting the active ingredients from significantly leaching from the target site.

The relative weight percentage of the cosmetic dye to the enhancing ingredient is about 1:2 to about 40:1. In one embodiment, the relative weight percentage of the cosmetic dye to the enhancing ingredient is about 10:1. The relative weight percentage of the active ingredients to water is about 1:5 to about 1:1000.

In one embodiment, the mammal is bovine livestock. The treatment of the livestock includes inhibiting disease, preventing disease, assisting in healing lesions, maintaining or improving hygiene, or combinations thereof. In one instance, the target site is the hoof the livestock. The livestock can be treated for hoof rot, foot rot, digital dermatitis and/or interdigital dermatitis. Typically, the livestock is treated by contacting the hoof of the livestock with a hoof bath comprising the aqueous composition. In another embodiment, the target site is the teat of the livestock and the disease is mastitis.

In one embodiment, the cosmetic dye is Gentian Violet, Brilliant Green, Toluidine Blue, or combinations thereof.

In one embodiment, the enhancing ingredient is selected from the group consisting of halogenated isothiazolin-3-ones; formaldehyde depot substances; chloracetamide; hexetidine; O-phenylphenol; 2,4-dichlorobenzylalcohol; trichlorcarban; glyoxal; chlorocresol, sodium hydroxymethylglycinate; sodium 2-biphenylate, chlorhexidine digluconate; chlorhexidine diacetate; hexamidine; phenoxyethanol; biphenyl-2-ol, formic acic, benzoic acid, salicylic acid, lactic acid, tannic acid, symclosene, sodium dichloroisocyanurate dehydrate, sorbic acid, methyl paraben; bronopol; triclosan; chlorhexidine; chlorhexidine digluconate, 5-isopropyl-2-methylphenol; 4-chloroxylol; DMDM-hydantoine; chlorophene, chloramin-T, benzylalcohol; cyanamide, phenoxyisopropanol; dimethyloxazolidine; benzylhemiformal; silver chloride, chlorobutanol; imazalil, sodium p-chloro-m-cresolate, diamine, troclosene sodium, phenol; herbal extracts, thymol, menthol, rosemary oil, carvacrol, magnolia bark extract and synthetics.

In one aspect, the present invention provides a topical aqueous composition comprising: active ingredients comprising i) a cosmetic dye selected from a violet, blue or green dye, or combinations thereof, and ii) at least one enhancing ingredient, wherein the relative weight percentage of the cosmetic dye to the enhancing ingredient is about 2:1 to about 40:1, wherein the cosmetic dye interacts with keratinous material.

In one aspect, the present invention provides a topical aqueous composition comprising: i) water, and ii) active ingredients wherein the active ingredients consist essentially of an cosmetic dye selected from a violet, blue or green dye, or combinations thereof, and at least one enhancing ingredient, wherein the relative weight percentage of the cosmetic dye to the enhancing ingredient is about 1:2 to about 40:1, wherein the cosmetic dye interacts with keratinous material, and wherein the relative weight percentage of the active ingredients to water is about 1:5 to about 1:1000.

DETAILED DESCRIPTION OF THE INVENTION

The present invention provides aqueous concentrate compositions conveniently suitable for dilution into a use concentration, and the end use compositions; and methods to topically treat mammalian microbial disease and infection, and lesions and wounds resulting therefrom. The compositions and methods of the present invention enable killing a broad spectrum of bacteria, including Gram positive and Gram negative bacteria, while simultaneously inactivating or destroying viruses and fungi. The compositions are particularly effective against anaerobic bacteria, for example, *Arcanobacterium pyogenes*. The compositions are fast-acting and provide long-lasting efficacy.

Throughout this specification, quantities are defined by ranges, and by lower and upper boundaries of ranges. Each lower boundary can be combined with each upper boundary to define a range. The lower and upper boundaries should each be taken as a separate element.

In one embodiment, the active ingredients of the aqueous compositions of the present invention comprise i.) a violet, green or blue cosmetic dye, or combinations thereof, and ii.) at least one cosmetic preservative and/or antimicrobial (hereinafter "enhancing ingredient").

The cosmetic dye comprises a cationic nitrogen, wherein the cationic nitrogen is connected to a double bond of an aromatic carbon. The cationic nitrogen has bonds to only three carbon atoms, including one double bond to an aromatic carbon. This double bond to the cationic nitrogen can oscillate from one to all the other possible cationic nitrogen atoms in the molecule giving the molecule the color.

Examples of suitable violet, green and blue cosmetic dye include Gentian Violet, Brilliant Green and Toluidine Blue. These dyes can be 4-[(4-dimethylaminophenyl)-phenyl-methyl]-N,N-dimethyl-aniline; and (7-amino-8-methyl-phenothiazin-3-ylidene)-dimethyl-ammonium. Further examples include Brilliant Blue FCF, Ethyl Green, Green S, and Victoria Blue BO.

It has surprisingly been discovered that at a certain relative amount of the cosmetic dye to the enhancing ingredient, the antimicrobial efficacy of the component parts of the composition are synergistically enhanced. The preferred relative weight percentage of the cosmetic dye to the enhancing ingredient has a range of about 1:2 to about 40:1 (or of about 2:1 to about 40:1). Examples of other preferred lower boundaries of this range include 5:1; 10:1, 15:1 and 20:1. Examples of other preferred upper boundaries of this range include 20:1; 25:1; 30:1 and 35:1.

In the aqueous compositions of the present invention, the relative weight percentage of the active ingredients to water is about 1:5 to about 1:1000, or about 1:25 to about 1:1000. Examples of other preferred lower boundaries of this range include about 1:10; about 1:100; 1:200 and 1:500. Examples of other preferred upper boundaries of this range include 1:500; 1:750; and 1:900.

For example, in a preferred embodiment, the aqueous composition contains approximately a maximum of 3 wt. % active ingredients and 97 wt. % water. For instance, the active ingredients can be 0.31 wt. % of the aqueous composition, of which 0.2 wt. % is the violet, green or blue cosmetic dye and 0.01 wt. % is the enhancing ingredient and 0.1% is a stabilizer. Accordingly, in such example, the corresponding amount of water is about 99.69 wt. % so that the actives to water ratio is about 0.31:99.69 or 1:322.

In some embodiments, the compositions of the present invention can further comprise a gelling and/or thickening agent wherein the ratio of the active ingredients to the agent is about 2:1 to 1 to 40. Examples of such agents include gums, xanthem gum, cellulose, methylcellulose, carboxymethylcellulose, chitosan, alginates, polysaccharides, their derivatives and combinations thereof.

In a preferred embodiment, the compositions do not include quaternary ammonium compounds. (In quaternary ammonium compounds, the cationic nitrogen has four separate bonds to four carbon atoms.) Also, in a preferred embodiment, the compositions also do not include and/or do not include an anticoagulant and/or do not include peroxides and/or do not include heavy metal based antimicrobials. Some examples of anticoagulants include heparin, hirudin, EGTA, urokinase, streptokinase, and hydrogen peroxide. Some examples of heavy metal based antimicrobials include copper sulfate and zinc sulfate. In a preferred embodiment, the compositions do not include cosmetic preservatives based on an organic acid except for tannic acid.

Accordingly, the synergistic combination of the i) cosmetic dye and ii) the enhancing ingredient(s) decrease the minimum inhibitory concentration (MIC) of each individual component. Also, the active ingredients of the present invention are effective at a much lower concentration than the active ingredients of other antimicrobial compositions which use dyes or cosmetic preservative compounds; and are effective at a much lower concentration than heavy metal based antimicrobials.

Additionally, the combination of the cosmetic dye and the enhancing ingredient(s) increase the spectrum of microbes that each component could individually target. The compositions of the present invention enable killing a broad spectrum of bacteria, including Gram positive and Gram negative bacteria such as *S. aureus, S. choleraesuis, E. coli, K pneumoniae*, and anaerobic bacteria, such as, for example, *Arcanobacterium pyogenes* while simultaneously inactivating or destroying viruses and fungi. The cosmetic dyes suitable for the compositions are dyes which interact (e.g., bind) with keratinous material when acting synergistically with the enhancing ingredients of the present invention.

The topical antimicrobial composition can be in the form of a concentrate for ease of transport. Preferably, in the concentrate, and consequently in the diluted ready-to-use form, the active ingredients to water are at about 1:5 to 1:500 or 1:1000. A preferred concentrate has about 10 wt. % dye and about 2 wt. % specific cosmetic preservative. Such a concentration makes shipping very economically. Further examples include a concentrate having a ratio of about 1:9 (actives to water). In the diluted form, the composition has a typical ratio of about 0.2 to 99.8, that is, of about 2 to 998 or about 1:500. Typical other ready to use ratios include about 1:100 or 1:200 or about 1:300, up to about 1:1000.

The aqueous composition is fast-acting and long-lasting. In particular, the aqueous composition quickly penetrates porous keratinous material (e.g., keratinous material of skin tissue, hooves, finger/toe nails, and hair). Once the site of interest (i.e., the target site) is in contact with the composition for few seconds, the cosmetic dye interacts with the keratinous material of a mammal in such a way that it is resistant to leaching.

Because the composition is resistant to leaching, the duration of the antimicrobial activity is increased. For example, at least about 90%, about 80%, about 70%, about 60%, about 50%, or about 40% of the composition remains at the target site despite exposure to percolating water. This property of the composition is very beneficial when applied to bovine livestock since such animals are typically exposed to environmental water, for example, while grazing.

Additionally, the cosmetic dye substantially stains the target site. Such staining is a useful property of the compositions. For example, the dye indicates the presence of the active ingredients, and their penetration depth; that is, the protected zone is clearly elucidated. Using this indicator feature of the composition, it has been demonstrated that even after extensive exposure to percolating water, the depth of penetration of the composition and its intensity of staining are not diminished.

In one embodiment, the active ingredients of the present invention consists essentially of (or consists of) a cosmetic dye and at least one enhancing ingredient. That is, other ingredients that may materially affect the basic and novel characteristics of the active ingredients of the invention are specifically excluded from the composition. The active ingredients are the cosmetic dye(s) and the enhancing ingredient(s) of the compositions of the invention (e.g., aqueous composition), or the primary antimicrobial ingredients of the compositions of the invention (e.g., aqueous composition). Preferably, such composition also includes a stabilizer.

A typical pH range of the aqueous compositions of the present invention is from about 2.5 to 7. A typical pH range for a concentrate of the compositions is about 2.8 to 3. The end user typically may make about 2% to 5% aqueous solution for a hoof bath. Such a solution typically has a pH of slightly below about 3.5. In actual use, when cows walk through a 2% hoof bath and drop manure, the pH typically gradually rises to above about 4. A pH of below about 7 does not typically decrease the efficacy of the compositions.

In another embodiment, the present invention includes a method of treating mammals by topically applying the compositions to desired target sites. In this specification "treating" refers to inhibiting disease; preventing disease; aiding in the prevention of disease; assisting in healing lesions; maintaining or increasing the hygiene level, or combinations thereof. Typical target sites include sites on the body that are susceptible to microbial infection and are prone to lesions and wounds. The diseases which can be treated by the methods of the present invention include any microbial infections; lesions or wounds that result from such infections; and lesions or wounds that are vulnerable to such infections.

In embodiments, where compositions of the present invention are in the form of a gel, the gel is dabbed onto a target site, and optionally, a bandage may be applied.

The invention is particularly well suited for treating bovine mammals, in particular, bovine livestock. Examples of bovine mammals include cows, cattle, and ox, The compositions are also suitable for ovine, caprine, hircine and corvine animals, such as, for example, sheep, goat, deer, yak, buffalo, antelope, bison, deer and elk. Examples of diseases which can be treated include diseases related to hooves, including, for example, hoof rot, digital dermatitis, interdigital dermatitis, foot rot, strawberry disease (Mortellaro disease) and/or bacterial, viral and fungal infections.

Another disease of dairy animals that can be treated by the methods of the invention is mastitis. Mastitis is one of the most common and economically costly diseases confronting milk producers. Economic losses result from poor milk quality, lower milk production, and potential culling of chronically infected animals.

The method of applying the composition depends on the disease and the target sites. For example, the composition can be sprayed, brushed, dabbed, or flooded onto the susceptible sites, such as, for example, hooves, skin, hair, and the udder.

One common application mode for hoof diseases is a hoof bath or a foot bath. For example, the composition can be used in such a way that animals walk through the composition, thereby preventing the spread of microorganisms, and also providing an opportunity to treat any infections on the hooves of the animals. Alternatively, the composition can be formulated and applied such that farm workers walk through the composition and thereby prevent microorganisms on their boots from spreading.

The compositions of the present invention have a biodegradation time of about two weeks. Thus, hoof/foot baths using these compositions in conjunction with biogasgenerators is quite valuable, since they do not impair the biogas generation. Copper sulfate is not suitable for such use because of its long term influence on the digester system stopping the biogas production, in addition to their negative environmental impact.

One common application mode for treating mastitis is a teat dip. The composition is placed in a small container with a shape adapted to the teat. The teat is then dipped into the container filled with the composition. Another application mode is spraying the udder including the teats.

"Enhancing Ingredients"

Preferably, the enhancing ingredients include cosmetic preservative(s) and/or antimicrobials, such as, for example, halogenated isothiazolin-3-ones; formaldehyde depot substances; chloracetamide; hexetidine; O-phenylphenol; 2,4-dichlorobenzyl-alcohol; trichlorcarban; glyoxal; sodium hydroxymethyl-glycinate; chlorhexidine digluconate; chlorhexidine diacetate; hexamidine; phenoxyethanol; methyl paraben; bronopol; triclosan; chlorhexidine; 5-isopropyl-2-methylphenol; 4-chloroxylol; DMDM-hydantoine; benzyl-alcohol; phenoxyisopropanol; dimethyloxazolidine; benzyl-hemiformal; chlorobutanol; phenol; and herbal extracts and/or synthetics, for example, thymol, menthol, rosemary oil, carvacrol, and the like.

Other example of preferred enhancing ingredients (i.e., specific cosmetic preservative(s) and/or antimicrobials) is/are chlorocresol; sodium 2-biphenylate; biphenyl-2-ol; formic acid; benzoic acid; salicylic acid; lactic acid; tannic acid;

symclosene; sodium dichloroisocyanurate dehydrate; sorbic acid; chlorhexidine digluconate; chlorophene; chloramin-T; cyanamide; silver chloride; imazalil; sodium p-chloro-m-cresolate; diamine; troclosene sodium; and magnolia bark extract Auxiliary Substances In addition to the active components, the above mentioned compositions can include other, non-toxic auxiliary agents, as long as such agents do not detract from the benefits provided by the present therapeutic compositions. These agents can, for example, facilitate the delivery and efficiency of the therapeutic agent and/or stabilize the composition (e.g., cosmetic stabilizers) with respect to its shelf life or its actual outdoor applications. The preferred range of these agents in the composition is about 0.05% to 12%.

For example, these compositions can contain water-soluble skin conditioning or moisturizing agents that do not interfere with the synergistic antimicrobial properties of the compositions. Examples of these ingredients are glycerin; glycols; polyols, such as polyethylene glycol; lanolin; aloe vera, grapefruit seed extract, and vitamins, such as E, C and A. These agents serve to assist in soothing and retaining moisture on the skin. Examples of stabilizing agents (i.e., stabilizers) include cosmetic stabilizers; radical scavengers; antioxidants; and UV absorbers e.g., cinnamate derivatives, benzophenone derivatives, vitamins and the like.

Agents such as colorants, fragrances and insect repellants (e.g., citronella) may also be included in the composition. Other examples of agents include preservatives, excipients, pH buffering agents, alcohols, chelating agents (e.g., EDTA), film-forming or barrier forming hydrophilic binder combinations (e.g. polyurethanes and polyvinyl pyrrolidone) or other therapeutics that do not contaminate meat or dairy products produced by the animal, and mixtures thereof.

Carrier agents can also be included in the aqueous composition of the present invention. However, typically, the composition is used without being placed on, or in, a substrate. For example, the composition is not placed onto a polyurethane polymer and/or not used in moldable/pliable compositions. An example of a moldable/pliable composition is a composition which comprises flour.

EXAMPLES

Digital dermatitis, mastitis and other related microbial infections in animals can effectively be treated by a topical application of an aqueous formulation containing specific combinations of antimicrobial dyes and specific cosmetic preservative compound(s). The general composition comprises, or consists essentially of, the following:

Example 1

0.001 to 2 wt. % of Gentian Violet
0.001 to 0.1% of triclosan
0.01 to 0.2 wt % of UV absorber;
Rest Water.

Example 2

0.001% to 1% Brilliant Green;
0.001% to 1% Toluidine blue
0.005% to 0.5% Phenoxyethanol;
Rest water.

Example 3

Sprayable sanitizer teat dip:
0.05 to 0.5 wt. % Brilliant Green;
0.005% to 0.05 wt. % Phenoxyethanol;
3% to 15 wt. % Ethanol;
0.01% to 0.8 wt. % Polyurethane;
0.005% to 0.3 wt. % Polyvinyl pyrrolidone;
0.1% to 0.3 wt. % Yellow 5 Dye.
Rest water Example 4

0.05 to 0.5 wt. % Brilliant Green;
0.005% to 0.05 wt. % Phenoxyethanol;
Rest water
MIC Test against Enterococcus hirae according to JACh 48 (2001)

The minimum inhibiting concentration of the combination solution against *E. hirae* was determined to be less than 0.05% with a 100% of organism reduction. Growth was observed at 0.005%. In conclusion the MIC is expected to be between 0.005% to 0.05%

Example 5

MIC Test of example 4 against *Arcanobacterium pyogenes* (ATCC#9731 and ATCC#19411) under anaerobic conditions were conducted by the TOXIKON. A 100% reduction and a log-reduction of 6.63 was found at the concentration of <0.0098% for both strains.

Example 6

Comparative Test

Under the same conditions as mentioned in Example 5 conducted by TOXIKON the MIC of a 10% copper sulfate solution (commonly used in hoof baths worldwide) was determined. Against *Arcanobacterium pyogenes*, Strain ATCC#9731 and ATCC#19411 also under anaerobic conditions it was found that the 10% copper sulfate solution at the 8-times concentration, that means it has kill rate of close to 100% when the concentration is at least 0.078%.

Conclusion: In order to control the anaerobic organism *Arcanobacterium pyogenes*, a required concentration of at least 8-times of a 10% copper solution is needed in comparison to a solution according to example 4.

Example 7

Comparative Example

Hoof samples were submerged for 15 seconds in (1) the composition of the invention (i.e., 4:1 of cosmetic dye: Phenoxyethanol, total amount about 0.3 wt. %); (2.1) a 10 wt. % copper sulfate (2.2) a 10 wt. % zinc sulfate solution; (3) untreated as a control. The samples were then washed for two hours to simulate leaching. The samples were then placed into melted PA agar to solidify. Melted agar containing 10E5 CFU/ml of *T. mentagrophytes* was then added and incubated at room temperature for 3 and 6 days. The copper and zinc sulfate treated samples, as well as the controls, showed intense microbial growth. The hoof sample treated with the composition of the invention had a clear zone of inhibition, about 12 mm in radius and fewer microbial colonies around the hoof.

Example 7A

Comparative Example

Hoof samples were submerged for 15 seconds in (1) the composition of the invention (i.e., 4:1 of antimicrobial dye:Phenoxyethanol, total amount about 0.21 wt. % or 0.3 wt. %); (2) a 10 wt. % copper sulfate or 10 wt. % zinc sulfate solution; or (3) untreated as a control. The samples were then washed for two hours to simulate leaching. The samples were then placed into melted PA agar to solidify. Melted agar containing 10E5 CFU/ml of *T. mentagrophytes* was then added and incubated at room temperature for 3 and 6 days. The Copper/Zinc sulfate treated samples, as well as the controls, showed intense microbial growth. The hoof sample treated with the composition of the invention had a clear zone of inhibition, about 12 mm in radius and fewer microbial colonies around the hoof.

Example 8

0.01% to 2.1% Brilliant Green;
0.005% to 0.5% Benzylalcohol;
99.985% to 97.4% water.

Example 9

0.01% to 2.1% Brilliant Green;
0.005% to 0.5% Phenoxyethanol;
0.01% to 0.2% Benzophenone 4;
99.985% to 97.4% water.

Example 10

0.01% to 2.1% Brilliant Green;
0.005% to 0.5% Bronopol;
0.01% to 0.2% Ethylhexyl Methoxycinnamate;
99.985% to 97.4% water.

Example 11

0.01% to 2.1% Brilliant Green;
0.005% to 0.5% Glyoxal;
0.01% to 0.2% Hydrochinone;
99.985% to 97.4% water.

Example 12

0.05% Brilliant Green
0.1% Phenoxyethanol
0.2% Gentian Violet

Example 13

Comparative antimicrobial testing of example 4 with cosmetic dyes according to test method MCR 3.0 with actual hoof material Solution of Example 4 showed good hoof penetration ability with 100% growth inhibition on the hoof against bacteria and 100% growth inhibition on the hoof against fungi.

Toluidine Blue in aqueous solution ranging from 0.25 to 0.5% also had high hoof penetration ability but bacteria growth inhibition on the hoof was only 80% and fungi growth inhibition on the hoof only 50%

Gentian Violet in aqueous solution ranging from 0.25 to 0.5% also showed high hoof penetration ability, but bacteria growth inhibition on the hoof was only 90% and fungi growth inhibition was only 80%

Methylene Blue also in aqueous solution of 0.25 to 0.5% showed high hoof penetration ability but the growth inhibition against bacteria was only 60% and against fungi only 50%.

Example 14

0.5% Toluidine Blue
0.05% Brilliant Green
Rest water
Formulation showed excellent hoof penetration but bacteria and fungi growth inhibition was only 90%

Example 15

0.5% Methylene Blue
0.05% Brilliant Green
Rest water
Formulation showed excellent hoof penetration but only 60% bacteria growth inhibition and 80% fungi growth inhibition.

Example 16

0.5% Gentian Violet
0.05% Brilliant Blue
Rest Water
Formulation showed excellent hoof penetration and 100% growth inhibition on the hoof against bacteria and fungi.

Example 17

0.5% Brilliant Green
0.625% EDTA
Rest water
Formulation showed good penetration into the hoof but only 80% growth inhibition on the hoof against bacteria and fungi.

Example 18

0.05% Brilliant Green
Rest water

Formulation does not provide an inhibition activity on the hoof surface.

Example 19

0.05% Brilliant Green
0.1% Phenoxyethanol
0.2% Gentian Violet
Rest water

The formulation was tested in comparison to formulation of Example 4 and compared with an untreated control. The control showed no inhibition against *Escherichia coli, Staphylococcus aureus* and fungi. Formulation of Example 4 showed complete inhibition against *E. coli, S. aureus* and fungi.

Formulation of Example 19 also showed complete inhibition against *E. coli, S. aureus* and fungi.

Example 20

0.5% Toluidine Blue
Rest water

Formulation shows excellent penetration into the hoof in 15 sec but exhibits only 80% bacterial growth inhibition and 50% fungi growth inhibition.

Example 21

0.5% Toluidine Blue
0.05% Grapefruit seed extract
Rest water

Formulation shows excellent penetration into the hoof in 15 sec. The bacteria and fungi growth inhibition was 100%

Example 22

0.1% Grapefruit seed extract
Rest water

Formulation showed only 60% bacteria growth inhibition and 80% fungi growth inhibition.

Example 23

According to standard method EN 14349 (Chemical disinfectants and antiseptics Quantitative surface test for the evaluation of bacterial activity of chemicals disinfectants and antiseptics used in veterinary field on non-porous surfaces without mechanical action) the Example 4 was tested against the Gram-negative organisms *Pseudomonas aeruginosa* and *Proteus vulgaris* as well as the Gram-positive *Staphylococcus aureus* and showed in the eradicating application rate of 5% a reduction rate of 10000 (4 log)

Example 24

1% Tannic acid
0.2% Toluidine Blue
Rest Water

Formulation showed no growth on a hoof surface where as 0.2% Toluidine Blue alone showed bacterial growth on a hoof surface.

Example 25

The objective was to evaluate the relative efficacy of a novel, commercially available disinfectant agent (T-Hexx Dragonhyde HBC, Hydromer, Branchburg, N.J.) compared with formalin and copper sulfate. The hypothesis was 2 sided; therefore, the hypothesis was that the new agent would be better or worse compared with the industry gold standard footbath agents, formalin and copper sulfate. The study was conducted in a large commercial dairy farm. Two identical studies were conducted, the first comparing Dragonhyde (5% solution, twice weekly) and formalin (5% solution, twice weekly) and the second comparing Dragonhyde (5% solution, twice weekly) and copper sulfate (10% solution, twice weekly). The study design was identical for both studies with 4 pens (physically identical), 2 treatments (Dragonhyde vs. formalin and Dragonhyde vs. copper sulfate), 2 periods (crossing over the treatment within pen), and 3 repeated measures (3 observations per cow: enrollment, wk 2, and wk 4). For study 1, 406 cows were enrolled (n=201 formalin and 205 Dragonhyde). For study 2, 356 cows were enrolled (n=189 copper sulfate and 167 Dragonhyde). The adjusted odds of digital dermatitis lesion (DDL) throughout the study period were analyzed by mixed logistic regression model. In study 1, the odds of DDL were 1.36 times higher for the formalin group compared with the Dragonhyde group. In study 2, the data were analyzed by a similar statistical model and the variable treatment did not significantly affect the overall prevalence of DDL. In conclusion, the performance of 3 hoof care products was evaluated and it was concluded that Dragonhyde performed better than formalin and that there was no difference between copper sulfate and Dragonhyde.

In one aspect, the present invention provides a method of treating a mammal comprising topically applying an aqueous composition to a target site on the mammal, wherein the aqueous composition comprises active ingredients comprising an antimicrobial dye and specific cosmetic preservative compound(s) (i.e., specific cosmetic preservative(s)). The relative weight percentage of the antimicrobial dye to the specific cosmetic preservative(s) is about 2:1 to about 40:1. The antimicrobial dye interacts with keratinous material thereby i) substantially staining the target site and ii) inhibiting the active ingredients from significantly leaching from the target site.

In one embodiment, the relative weight percentage of the antimicrobial dye to the specific cosmetic preservative(s) is about 20:1. In one embodiment, the relative weight percentage of the active ingredients to water is about 1:25 to about 1:1000.

In one embodiment, the mammal is bovine livestock. The treatment of the bovine livestock comprises inhibiting disease, preventing disease, assisting in healing lesions, or combinations thereof. In one instance, the target site is the hoof the livestock. The livestock can be treated for hoof rot, digital dermatitis and/or interdigital dermatitis. Typically, the livestock is treated by contacting its hoof with a hoof bath comprising the aqueous composition. In another embodiment, the target site is the teat of the livestock and the disease is mastitis.

In certain embodiments, the antimicrobial dye can be a triarylmethane dye, a monoazo dye, a diazo dye, an indigoid dye, a xanthene or a fluorescein dye, an anthraquinone dye, or a quinoline dye. Preferably, the antimicrobial dye is a triphenylmethane dye. Examples of preferred triphenylmethane dyes include N-[4[Bis[4-(dimethylamino)-phenyl]methylene]-2,5-cyclohexadien-1-ylidene]-N-methyl-methanaminium chloride (i.e., Gentian Violet or Crystal Violet); N-[4-[[4-(Diethylamino)phenyl]-phenylmethylene]-2,5-cyclohexadien-1-ylidene]-N-ethylethanaminium sulfate (1:1) (i.e., Brilliant Green); and Malachite Green.

The activity of triphenylmethane dyes is particularly enhanced by the synergistic combination with the specific cosmetic preservatives of the present invention. In particular, triphenylmethane dyes are known to have poor light stability and tend to be decolorized by bacteria (see, Jones, J. J. and Falkinham, J. III, Antimicrobial Agent and Chemotherapy, 47(7):2323 (2003)). Also, a high concentration of these triphenylmethane dyes is typically needed to achieve the expected functions due to their high minimum inhibition concentration (MIC). Moreover, triphenylmethane dyes are typically are only effective for Gram positive bacteria. However, the synergistic combination with the specific cosmetic preservatives enables triphenylmethane dyes to overcome their limitations. The triphenylmethane dyes become more light stable, have a lower MIC, and become capable of inhibiting the activities of Gram negative bacteria, viruses and fungi, in addition to inhibiting the activity of Gram positive bacteria.

In one embodiment the specific cosmetic preservative(s) is/are halogenated isothiazolin-3-ones; formaldehyde depot substances; chloracetamide; hexetidine; O-phenylphenol; 2,4-dichlorobenzylalcohol; trichlorcarban; glyoxal; sodium hydroxymethylglycinate; chlorhexidine digluconate; chlorhexidine diacetate; hexamidine; phenoxyethanol; methyl paraben; bronopol; triclosan; chlorhexidine; 5-isopropyl-2-methylphenol; 4-chloroxylol; DMDM-hydantoine; benzylalcohol; phenoxyisopropanol; dimethyloxazolidine; benzylhemiformal; chlorobutanol; phenol; and herbal extracts, for example, thymol, menthol, rosemary oil, carvacrol and the like.

In one aspect, the present invention provides a topical aqueous composition comprising active ingredients comprising an antimicrobial dye and at least one specific cosmetic preservative wherein the relative weight percentage of the antimicrobial dye to the specific cosmetic preservative(s) is about 2:1 to about 40:1. The antimicrobial dye interacts with keratinous material. Preferably, the relative weight percentage of the antimicrobial dye to the specific cosmetic preservative(s) is about 20:1. Preferably, the relative weight percentage of the active ingredients to water is about 1:25 to about 1:1000. Preferably, the antimicrobial dye is a triphenylmethane dye. Preferably, the triphenylmethane dye is Gentian Violet, Brilliant Green and Malachite Green.

Preferably, specific cosmetic preservatives include halogenated isothiazolin-3-ones; formaldehyde depot substances; chloracetamide; hexetidine; O-phenylphenol; 2,4-dichlorobenzylalcohol; trichlorcarban; glyoxal; sodium hydroxymethylglycinate; chlorhexidine digluconate; chlorhexidine diacetate; hexamidine; phenoxyethanol; methyl paraben; bronopol; triclosan; chlorhexidine; 5-isopropyl-2-methylphenol; 4-chloroxylol; DMDM-hydantoine; benzylalcohol; phenoxyisopropanol; dimethyloxazolidine; benzylhemiformal; chlorobutanol; phenol; and herbal extracts, for example, thymol, menthol, rosemary oil, carvacrol and the like.

Additionally, the composition may contain cosmetic stabilizers, radical scavengers, and UV absorbers e.g. cinnamate derivatives, benzophenone derivatives, vitamins and the like.

In one aspect, the present invention provides a topical aqueous composition comprising water and active ingredients wherein the active ingredients consist essentially of: an antimicrobial dye and at least one specific cosmetic preservative. The relative weight percentage of the antimicrobial dye to the specific cosmetic preservative(s) is about 5:1 to about 40:1. The antimicrobial dye interacts with keratinous material. The relative weight percentage of the active ingredients to water is about 1:25 to about 1:1000. Preferably, the relative weight percentage of the antimicrobial dye to the specific cosmetic preservative(s) is about 20:1.

The invention claimed is:

1. A method of treating hoof rot, foot rot, digital dermatitis and/or interdigital dermatitis in a hoofed mammal comprising
contacting the hoof of the mammal in need thereof, with a hoof bath comprising an aqueous composition, wherein the aqueous composition consists of:
active ingredients consisting of
   i) Brilliant Green, and
   ii) benzoic acid, and
   water,
wherein the relative weight percentage of the Brilliant Green to the benzoic acid is about 20:1 to about 40:1,
wherein the relative weight percentage of the active ingredients to water is about 1:100 to about 1:1000,
wherein the Brilliant Green interacts with keratinous material thereby i) substantially staining the target site and ii) inhibiting the active ingredients from significantly leaching from the target site.

2. The method of claim 1 wherein the mammal is bovine livestock.

3. A method of treating hoof rot, foot rot, digital dermatitis and/or interdigital dermatitis in a bovine mammal comprising:
a) adding active ingredients to water to form a hoof bath, wherein the active ingredients consists of (i) Brilliant Green, and (ii) benzoic acid,
wherein the relative weight percentage of the active ingredients to water is about 1:100 to about 1:1000; and
b) contacting hooves of the mammal in need thereof, with the hoof bath, wherein Brilliant Green interacts with keratinous material thereby staining the hooves,
wherein the weight percentage of Brilliant Green in the hoof bath is from about 0.01% to 2.1%, and the weight percentage of benzoic acid in the hoof bath is about 0.005% to 0.5%, wherein the lower boundary of the relative weight percentage of the Brilliant Green to benzoic acid is about 20:1.

* * * * *